(12) United States Patent
Marhold et al.

(10) Patent No.: US 7,847,096 B2
(45) Date of Patent: Dec. 7, 2010

(54) 4-AMINOPHENYLMORPHOLINONE DERIVATIVES AND THEIR PREPARATION

(75) Inventors: Albrecht Marhold, Leverkusen (DE); Wolfgang Ebenbeck, Leverkusen (DE)

(73) Assignee: Saltigo GmbH, Leverkusen (DE)

( * ) Notice: Subject to any disclaimer, the term of this patent is extended or adjusted under 35 U.S.C. 154(b) by 867 days.

(21) Appl. No.: 11/664,971

(22) PCT Filed: Oct. 1, 2005

(86) PCT No.: PCT/EP2005/010625

§ 371 (c)(1),
(2), (4) Date: Apr. 9, 2007

(87) PCT Pub. No.: WO2006/042634

PCT Pub. Date: Apr. 27, 2006

(65) Prior Publication Data

US 2009/0018126 A1    Jan. 15, 2009

(51) Int. Cl.
*C07D 295/08* (2006.01)
*A61K 31/535* (2006.01)

(52) U.S. Cl. .................................. 544/170; 514/231.5
(58) Field of Classification Search .................. 544/170
See application file for complete search history.

(56) References Cited

U.S. PATENT DOCUMENTS 7,034,017 B2    4/2006  Straub et al.
7,157,456 B2    1/2007  Straub et al.

FOREIGN PATENT DOCUMENTS

WO    WO2004/033450    4/2004

OTHER PUBLICATIONS

Morissette et al. High-throughput crystallization: polymorphs, salts, co-crystals and solvates of pharmaceutical solids. Adv. Drug Del. Rev. 56, 275-300 (2004).*
Vippagunta et al. Crystalline solids. Adv. Drug Del. Rev. 48, 3-26 (2001).*

* cited by examiner

*Primary Examiner*—Frederick Krass
*Assistant Examiner*—Sara E Clark
(74) *Attorney, Agent, or Firm*—Michael A. Miller

(57) ABSTRACT

The invention relates to novel aminophenylmorpholinone derivates (I)

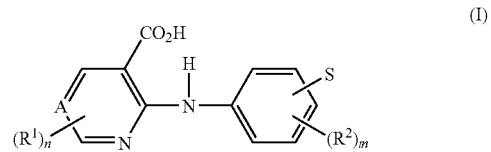

in which S represents an optionally substituted morpholinone radical, to a process for their preparation and to their use.

10 Claims, No Drawings

4-AMINOPHENYLMORPHOLINONE DERIVATIVES AND THEIR PREPARATION

This application is a national stage application under 35 U.S.C. §371 of international application PCT/EP05/10625, filed Oct. 1, 2005, claiming benefit of foreign priority to German application 10 2004 050 283.8, filed Oct. 15, 2004.

The invention relates to novel aminophenylmorpholinone derivatives, to a process for their preparation and to their use.

4-(morpholin-4-yl)aniline or 4-(3-oxomorpholin-4-yl) aniline are important building blocks for the preparation of pharmaceutically active compounds.

From WO-A 2004/033450 it is known, for example, that the compound 6-methyl-2-[4-(4-morpholino)aniline]nicotinic acid, by virtue of its inhibiting effect on the replication of the hepatitis C virus, is suitable as pharmaceutically active compound for treating hepatitis C. However, with respect to effectiveness, solubility for a suitable administration form and in pharmacokinesis, the compound has disadvantages.

Accordingly, there is still a need for active compounds which do not have the abovementioned disadvantages and are suitable for the therapeutic treatment of, for example, viral diseases, in particular hepatitis C.

Accordingly, it was the object of the present invention to provide such compounds.

Surprisingly, it has now been found that pyrimidine- and pyridinecarboxylic acid derivatives which are substituted in the 2- or 4-position by an optionally substituted 4-(3-oxomorpholin-4-yl)aniline radical meet these requirements.

Accordingly, the present invention provides compounds of the general formula (I)

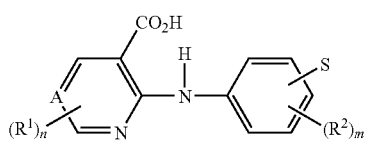

in which
A represents CH, CR$^1$ or N, preferably CH,
R$^1$ independently of one another represent H, OH, C$_1$-C$_4$-alkyl, partially fluorinated or perfluorinated C$_1$-C$_4$-alkyl, C$_1$-C$_4$-alkoxy, partially fluorinated or perfluorinated C$_1$-C$_4$-alkoxy, amino, mono- or diamino-C$_1$-C$_4$-alkyl, nitro, carboxyl, C(S)NH$_2$, C(O)NH$_2$, cyano or halogen,
n represents 0, 1 or 2,
R$^2$ independently of one another represent H, OH, C$_1$-C$_4$-alkyl, partially fluorinated or perfluorinated C$_1$-C$_4$-alkyl, C$_1$-C$_4$-alkoxy, partially fluorinated or perfluorinated C$_1$-C$_4$-alkoxy, amino, mono- or diamino-C$_1$-C$_4$-alkyl, nitro, carboxyl, C(S)NH$_2$, C(O)NH$_2$, cyano or halogen,
m represents 0, 1, 2, 3 or 4,
Z represents a radical selected from the general formulae (II-a) to (II-d)

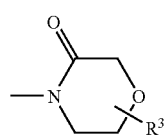

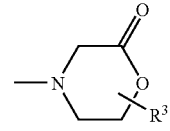

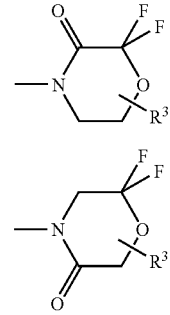

in which
R$^3$ represents H, C$_1$-C$_4$-alkyl, optionally substituted C$_4$-C$_{24}$-aryl, preferably optionally substituted C$_6$-C$_{24}$-aryl, or optionally substituted C$_5$-C$_{18}$-aralkyl,
or salts of the compounds of the general formula (I) or solvates or hydrates of the compounds of the general formula (I) or their salts.

Salts of the compounds according to the invention can be physiologically acceptable salts of the compounds of the general formula (I) according to the invention with inorganic or organic acids.

Preference is given to salts with inorganic acids, such as, for example, hydrochloric acid, hydrobromic acid, phosphoric acid or sulphuric acid, or salts with organic carboxylic or sulphonic acids, such as, for example, acetic acid, trifluoroacetic acid, propionic acid, maleic acid, fumaric acid, malic acid, citric acid, tartaric acid, lactic acid, benzoic acid or methanesulphonic acid, ethanesulphonic acid, benzenesulphonic acid, toluenesulphonic acid or naphthalenesulphonic acid.

Salts of the compounds according to the invention can also be physiologically acceptable salts of the compounds of the general formula (I) according to the invention with customary bases, such as, for example, alkali metal salts, such as, for example, sodium salts or potassium salts, alkaline earth metal salts, such as, for example, calcium salts or magnesium salts, ammonium salts, derived from ammonia or organic amines, such as, for example, diethylamine, triethylamine, ethyldiisopropylamine, procaine, dibenzylamine, N-methylmorpholine, dihydroabietylamine or methylpiperidine, or salts of ethanolamines, such as, for example, 2-diethylaminoethanol, 2-[(2-hydroxyethyl)methylamino]ethanol.

According to the invention, hydrates or solvates are those forms of the compounds of the general formula (I) according to the invention which, in the solid or liquid state, form a molecular compound or a complex by hydration with water or coordination with solvent molecules. Examples of hydrates are sesquihydrates, monohydrates, dihydrates or trihydrates. Also suitable are hydrates or solvates of salts of the compounds of the general formula (I) according to the invention.

Alkyl or alkoxy refers in each case independently to a straight-chain, cyclic, branched or unbranched alkyl or alkylene radical. This also applies to the non-aromatic moiety of an arylalkyl radical and to alkyl moieties of more complex substituents, such as, for example, mono- or diaminoalkyl.

$C_1$-$C_4$-Alkyl represents, for example, methyl, ethyl, n-propyl, isopropyl, n-butyl, sec-butyl, tert-butyl.

$C_1$-$C_4$-Alkoxy represents, for example, methoxy, ethoxy, n-propoxy, isopropoxy, n-butoxy, sec-butoxy, tert-butoxy.

Aryl represents in each case independently an aromatic radical having 4 to 24 carbon atoms in the skeleton, where no, one, two or three carbon atoms in the skeleton of each ring, but at least one carbon atom in the skeleton of the entire molecule, may be substituted by heteroatoms selected from the group consisting of nitrogen, sulphur and oxygen; however, aryl preferably represents a carbocyclic aromatic radical having 6 to 24 carbon atoms in the skeleton.

Examples of $C_6$-$C_{24}$-Aryl are phenyl, o-, p-, m-tolyl, naphthyl, phenanthrenyl, anthracenyl or fluorenyl, examples of heteroaromatic $C_4$-$C_{24}$-Aryl are those in which no, one, two or three carbon atoms in the skeleton of each ring, but at least one carbon atom in the skeleton of the entire molecule, may be replaced by heteroatoms selected from the group consisting of nitrogen, sulphur and oxygen, for example pyridyl, pyridyl N-oxide, pyrimidyl, pyridazinyl, pyrazinyl, thienyl, furyl, pyrrolyl, pyrazolyl, imidazolyl, thiazolyl, oxazolyl or isoxazolyl, indolizinyl, indolyl, benzo[b]thienyl, benzo[b]furyl, indazolyl, quinolyl, isoquinolyl, naphthyridinyl, quinazolinyl, benzofuranyl or dibenzofuranyl.

Arylalkyl represents in each case independently a straight-chain, cyclic, branched or unbranched alkyl radical according to the above definition which may be monosubstituted, polysubstituted or fully substituted by aryl radicals according to the above definition.

$C_5$-$C_{18}$-Arylalkyl represents, for example, benzyl or (R)- or (S)-1-phenylethyl.

Possible substituents for the radicals $R^3$ are numerous organic groups, for example alkyl, cycloalkyl, aryl, halogen, hydroxyl, ether, thioether, disulphide, sulphoxide, sulphonic acid, sulphonate, amino, aldehyde, keto, carboxylic ester, carbonate, carboxylate, cyano, alkylsilane and alkoxysilane groups, and also carboxamide groups.

Preferably, $R^1$ represents H, F, OH, methyl, methoxy, trifluoromethyl or difluoromethyl, particularly preferably H, F or methyl.

$R^2$ preferably represents H, F, Cl, CN, OH, methyl, methoxy, trifluoromethyl, difluoromethyl, $C(S)NH_2$ or $C(O)NH_2$, particularly preferably H, F or methyl.

$R^3$ preferably represents H, $C_1$-$C_4$-alkyl, optionally substituted phenyl or benzyl, particularly preferably H or methyl.

Preferably, Z is located in the p-position with respect to the amino substituent of the optionally substituted aminophenyl ring in the general formula (I).

In the context of the invention, all general or preferred radical definitions, parameters and illustrations given above and below can be combined with one another as desired, i.e. including combinations between the respective ranges and preferred ranges.

In preferred embodiments of the invention, $R^1$ and $R^2$ independently of one another represent H, F or methyl, and Z represents a radical of the general formula (II-a),

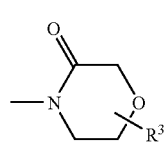

(II-a)

in which $R^3$ is H or methyl.

The compounds of the formulae (I-a) to (I-c) may be mentioned here by way of example.

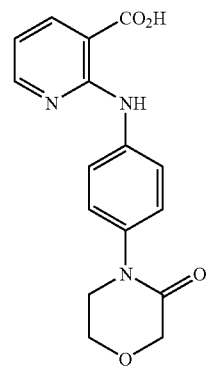

(I-a)

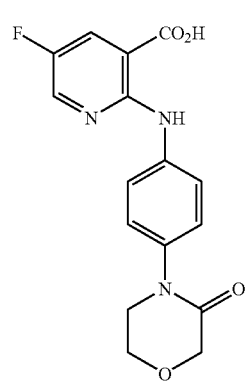

(I-b)

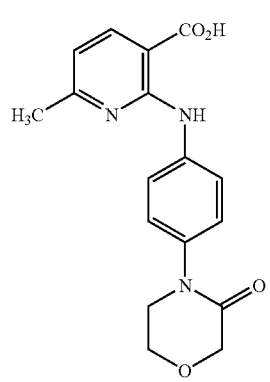

(I-c)

If the compounds of the general formula (I) according to the invention have a centre of chirality, the compounds of the general formula (I) according to the invention include, in the context of the invention, the individual enantiomers of these compounds in pure or enriched form, the racemates or mixtures of the individual enantiomers in any ratio.

The present invention also provides a process for preparing the compounds of the general formula (I) according to the invention which comprises reacting compounds of the general formula (III)

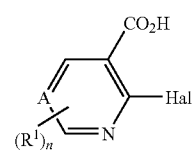

(III)

in which

Hal represents Cl, Br or I, preferably Cl or Br, particularly preferably Cl, and A and $R^1$ have the meaning given for the general formula (I) with compounds of the general formula (IV)

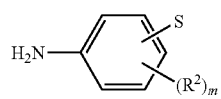

(IV)

in which $R^2$ and Z have the meaning given for the general formula (I).

The process according to the invention is, if appropriate, carried out in the presence of organic bases, such as, for example, aliphatic or aromatic amines or diamines. Preference is given to aromatic armines, such as, for example, pyridine, 2-methyl-, 3-methyl-, 4-methyl-, 2,4-dimethyl-, 3,4-dimethyl-, 3,5-dimethyl- or 2,6-dimethylpyridine, 5-ethyl-2-methylpyridine, 2-, 3- or 4-N,N-dimethylaminopyridine, N,N-dimethylaniline, N,N-dimethylbenzylamine or N-methylpiperidine, aliphatic amines, such as, for example, trimethylamine, triethylamine, triisopropylamine, tri-n-propylamine, tributylamine, diisopropylethylamine, N,N-dimethylcyclohexylamine, dicyclo-hexylamine, dicyclohexylethylamine, tri-n-octylamine, di-n-octylmethylamine, diamines, such as, for example, 1,3-dimethylimidazolidine or diazabicycloalkanes, such as, for example, 1,4-diazabicyclo[2.2.2]octane (DABCO), 1,5-diazabicyclo[4.3.0]non-5-ene (DBN), or 1,8-diaza-bicyclo[5.4.0]undec-7-ene (DBU).

The process according to the invention is preferably carried out in one or more solvents. Suitable solvents are, for example, organic solvents, such as alcohols, for example methanol, ethanol, n-propanol, isopropyl alcohol, n-, sec- or tert-butanol or amyl alcohol, ketones, for example, acetone, ethers, for example diethyl ether, methyl tert-butyl ether, dioxane or tetrahydrofuran, aliphatic or aromatic, optionally chlorinated hydrocarbons, for example dichloromethane, chloroform, 1,2-dichlorethane or toluene, xylene or carboxylic acid derivatives, for example acetonitrile or N,N-dimethylformamide, N,N-dimethylacetamide, N-methylpyrrolidone (NMP) or dimethylimidazolidinone (DMI), sulphones or sulphoxides, such as, for example, dimethyl sulphoxide (DMSO), or mixtures of two or more of these solvents. Particular preference is given to methanol, ethanol, isopropyl alcohol, dichloromethane, chloroform, acetone, acetonitrile, N,N-dimethylformamide, N,N-dimethylacetamide, N-methylpyrrolidone (NMP), dimethylimidazolidinone (DMI), dimethyl sulphoxide (DMSO).

The process according to the invention is preferably carried out at temperatures of from 40° C. to 150° C., particularly preferably from 40° C. to 110° C., very particularly preferably under reflux at the boiling point of the solvent or solvent mixture used. The reaction time is preferably from a number of hours to days, particularly preferably one to 15 days, very particularly preferably one to 10 days.

It may be advantageous to carry out the process according to the invention under an atmosphere of protective gas, such as, for example, a nitrogen or argon atmosphere; however, this is not necessarily required.

The process according to the invention can be carried out under atmospheric, elevated or reduced pressure, for example in the range from 0.5 to 5 bar. In general, it is carried out under atmospheric pressure.

The process according to the invention is carried out, for example, by reacting the compound of the general formula (III), the compound of the general formula (IV) and the organic base in the solvent(s) for the required reaction time by stirring under reflux. After cooling, for example to temperatures of from 10° C. to 30° C., preferably room temperature, the compound of the general formula (I) can be isolated after crystallization and filtration. If appropriate, the yield may be increased further by removing the solvent from the filtrate and taking up the residue in further solvent(s) and again completely or partially removing the solvent(s), if appropriate with subsequent crystallization. Suitable further solvents are those mentioned above, which, independently of the solvent(s) used for the reaction, may be identical to or different from these. For the isolation, it is preferred to use solvents different from those used for the reaction.

The compounds of the general formula (III) are commercially available. The compounds of the general formula (IV) can be prepared, for example, by known processes, as described, for example, in WO-A 01/47919 or WO-A 02/064575.

The compounds used in the process according to the invention of the general formula (IV),

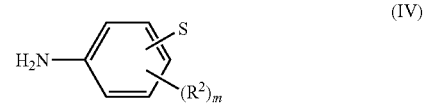

(IV)

in which $R^2$ has the meaning given for the compounds of the general formula (I) and Z represents a radical selected from the general formulae (II-b) to (II-d)

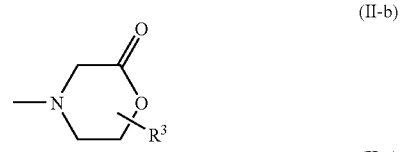

(II-b)

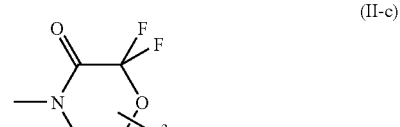

(II-c)

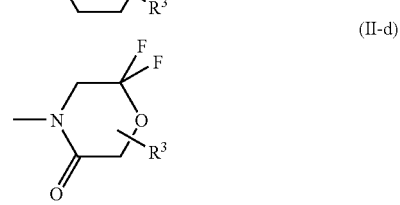

(II-d)

in which $R^3$ has the meaning given for the compounds of the general formula (I) are likewise novel and accordingly form part of the subject matter of the present invention.

The compounds of formula (IV-c) or (IV-d)

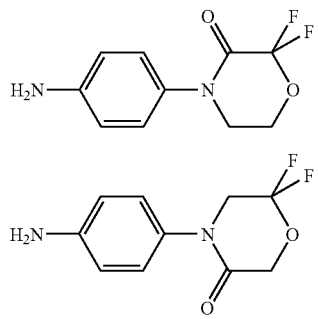

may be mentioned here by way of example.

These compounds of the general formula (IV) according to the invention are suitable for preparing pharmaceutically active compounds, both by the process according to the invention and by other processes. Thus, their use is not restricted to the use in the process according to the invention.

The compounds of the general formula (I) according to the invention and their salts, solvates and/or hydrates are suitable for use as pharmaceutically active compounds. The compounds of the general formula (I) according to the invention and their salts, solvates and/or hydrates exhibit an unforeseeable, useful pharmacological activity spectrum and are therefore suitable for treating disorders. In particular, the compounds of the general formula (I) according to the invention and their salts, solvates and/or hydrates have antiviral activity. With particular preference, they can be used for treating hepatitis C.

Suitable for application of the compounds of the general formula (I) according to the invention and their salts, solvates and/or hydrates are all customary application forms, such as, for example, orally, lingually, sublingually, buccally, rectally or parenterally, i.e. by circumventing the intestinal tract, and also intravenously, intra-arterially, intracardially, intracutaneously, subcutaneously, transdermally, intraperitoneally or intramuscularly.

The compounds of the general formal (I) according to the invention and their salts, solvates and/or hydrates can be converted in a known manner into the customary formulations, such as tablets, coated tablets, pills, granules, aerosols, syrups, emulsions, suspensions and solutions, using inert non-toxic pharmaceutically suitable carriers or solvents. Here, the therapeutically active compound according to the invention is preferably present in a concentration of from 0.1 to 95% by weight, particularly preferably from 0.5 to 90% by weight, of the total mixture, i.e. in amounts which are sufficient in order to achieve the dosage range indicated.

In spite of this, it may be necessary to depart from the amounts mentioned, namely depending on the body weight, on the type of administration route, on the individual response towards the medicament, on the type of formulation and on the time or interval at which administration takes place. Thus, in some cases it may be adequate to manage with less than the above-mentioned minimum amount, while in other cases the upper limit mentioned must be exceeded. In the case of the administration of relatively large amounts, it may be advisable to divide these into several individual administrations over the course of the day.

The present invention furthermore provides pharmaceutical formulations comprising at least one compound of the general formula (I) according to the invention or salts, solvates and/or hydrates thereof.

The formulations are prepared, for example, by extending the active compounds with solvents and/or carriers, using, if appropriate, emulsifiers and/or dispersants, where, for example if the solvent used is water, it may, if appropriate, be possible to use organic solvents as auxiliary solvents. Solvents, carriers, emulsifiers and dispersants suitable for this purpose are known to the person skilled in the art.

In general, the effective dose is, depending on the sex, the age and the physical state of the patient, for adults an amount of from 10 to 1000 mg/day, preferably from 20 to 500 mg/day, either in one or in a plurality of individual doses.

In spite of this, it may be necessary to depart from the effective doses mentioned, namely depending on the body weight, on the type of administration route, on the individual response towards the medicament, on the type of formulation and on the time or interval at which administration takes place. Thus, in some cases it may be adequate to manage with less than the abovementioned minimum amount, while in other cases the upper limit mentioned must be exceeded. In the case of the administration of relatively large amounts, it may be advisable to divide these into several individual administrations over the course of the day, either in several individual administrations or as a continuous infusion.

The compounds of the general formula (I) according to the invention and their salts, solvates and/or hydrates have particularly good solubility, which may be especially advantageous for certain administration forms.

The examples below serve to illustrate the invention in an exemplary manner and are not to be understood as limiting it.

EXAMPLES

Example 1

Preparation of 6-methyl-2-[4-(3-oxomorpholin-4-yl) phenylamino]nicotinic acid

Under an atmosphere of nitrogen protective gas, 4.30 g (25.0 mmol) of 2-chloro-6-methylnicotinic acid, 5.05 g (26.3 mmol) of 4-(4-aminophenyl)morpholin-3-one and 6 ml of pyridine in 90 ml of absolute $CHCl_3$ were stirred under reflux for 9 days. After complete conversion (the conversion was monitored by TLC), the reaction mixture was cooled to 20° C. and the residue was filtered off and washed with 30 ml of $CHCl_3$. Additionally, the filtrate was concentrated using a rotary evaporator, the oily residue was dissolved in 45 ml of $CH_2Cl_2$ and 20 ml of $CH_3OH$ were added. The $CH_2Cl_2$ was then removed under reduced pressure, which, after cooling the solution to 0° C., allowed further solid to be isolated, giving, together with the filter residue, a total of 4.48 g (13.7 mmol; 55%) of 6-methyl-2-[4-(3-oxomorpholin-4-yl)phenylamino]nicotinic acid as a yellow solid.

Melting point: 242-244° C.

$^1$H-NMR (DMSO-$d_6$), ppm: δ 2.44 ((s, 3H), 3.72 (t, 2H), 3.96 (t, 2H), 4.19 (s, 2H), 6.75 (dd, 1H), 7.32 (dd, 2H), 7.78 (dd, 2H), 8.13 (dd, 1H), 10.48 (s, 1H), 13.26 (br s, 1H)

The invention claimed is:

1. Compound of the general formula (I),

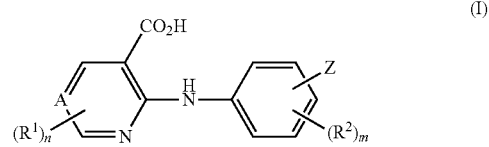

in which

A represents CH, $CR^1$ or N, $R^1$ independently of one another represent H, OH, $C_1$-$C_4$-alkyl, partially fluorinated or perfluorinated $C_1$-$C_4$- alkoxy, partially fluorinated or perfluorinated $C_1$-$C_4$-alkoxy, amino, mono- or diamino-$C_1$-$C_4$-alkyl, nitro, carboxyl, $C(S)NH_2$, $C(O)NH_2$, cyano or halogen, n represents 0, 1 or 2, $R^2$ independently of one another represent H, OH, $C_1$-$C_4$-alkyl, partially fluorinated or perfluorinated $C_1$-$C_4$-alkoxy, partially fluorinated or perfluorinated $C_1$-$C_4$-alkoxy, amino, mono- or diamino-$C_1$-$C_4$-alkyl, nitro, carboxyl, $C(S)NH_2$, $C(O)NH_2$, cyano or halogen, m represents 0, 1, 2, 3 or 4, Z represents a radical selected from the general formulae (II-a) to (II-d)

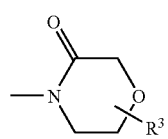
(II-a)

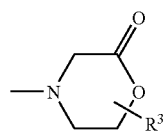
(II-b)

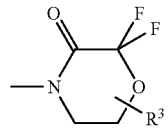
(II-c)

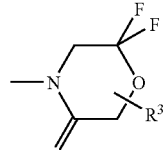
(II-d)

in which $R^3$ represents H, $C_1$-$C_4$-alkyl, optionally substituted $C_4$-$C_{24}$-aryl or optionally substituted $C_5$-$C_{18}$-aralkyl, or salts of the compounds of the general formula (I).

2. Compound according to claim 1, characterized in that $R^1$ represents H, F, OH, methyl, methoxy, trifluoromethyl or difluoromethyl.

3. Compound according to claim 1, characterized in that $R^2$ represents H, F, Cl, CN, OH, methyl, methoxy, trifluoromethyl, difluoromethyl, $C(S)NH_2$ or $C(O)NH_2$.

4. Compound according to claim 1, characterized in that
$R^1$, $R^2$ independently of one another represent H, F or methyl and
Z represents a radical of the general formula (II-a),

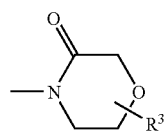
(II-a)

in which $R^3$ represents H or methyl.

5. Compound according to claim 1, characterized in that it is a compound selected from the formulae (I-a) to (I-c)

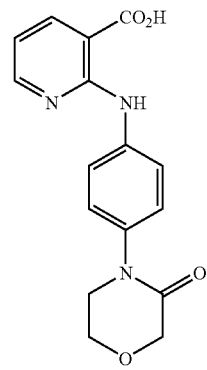
(I-a)

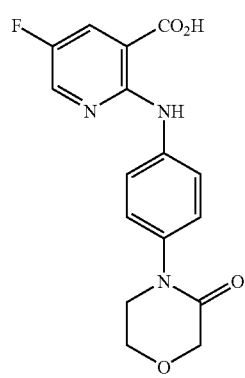
(I-b)

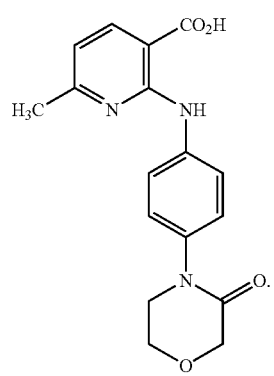
(I-c)

6. Compound of the general formula (IV),

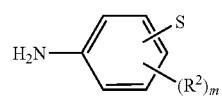
(IV)

characterized in that $R^2$ has the meaning given in claim 1 and Z represents a radical selected from the general formulae (II-b) to (II-d)

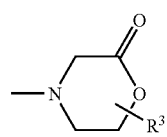
(II-b)

-continued

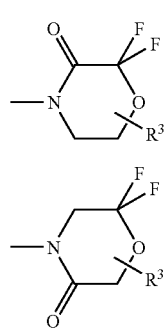
(II-c)

(II-d)

in which R³ has the meaning given in claim 1.

7. Compound according to claim 6, characterized in that it is the compound of the formula (IV-c) or (IV-d)

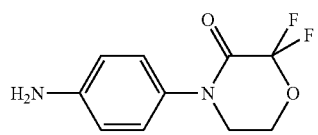
(IV-c)

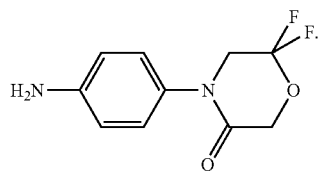
(IV-d)

8. Pharmaceutical formulation, comprising at least one compound according to claim 1.

9. Process for preparing compounds according to claim 1, characterized in that compounds of the general formula (III),

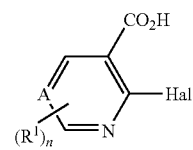
(III)

in which

Hal represents Cl, Br or I and

A and R¹ have the meaning given in claim 1 are reacted with compounds of the general formula (IV)

(IV)

in which R² and have the meaning given in claim 1.

10. Process according to claim 9, characterized in that Hal represents Cl.

* * * * *